(12) United States Patent
Machida

(10) Patent No.: US 10,531,789 B2
(45) Date of Patent: Jan. 14, 2020

(54) LIGHT-SOURCE DEVICE

(71) Applicant: OLYMPUS CORPORATION, Hachioji-shi, Tokyo (JP)

(72) Inventor: Ryo Machida, Kanagawa (JP)

(73) Assignee: OLYMPUS CORPORATION, Tokyo (JP)

(*) Notice: Subject to any disclaimer, the term of this patent is extended or adjusted under 35 U.S.C. 154(b) by 521 days.

(21) Appl. No.: 15/433,584

(22) Filed: Feb. 15, 2017

(65) Prior Publication Data

US 2017/0156577 A1    Jun. 8, 2017

Related U.S. Application Data

(63) Continuation of application No. PCT/JP2015/072634, filed on Aug. 10, 2015.

(30) Foreign Application Priority Data

Aug. 20, 2014   (JP) .................................. 2014-169408

(51) Int. Cl.
*A61B 1/06*   (2006.01)
*G02B 6/293*  (2006.01)
*G02B 23/24*  (2006.01)

(52) U.S. Cl.
CPC .............. *A61B 1/06* (2013.01); *A61B 1/0646* (2013.01); *A61B 1/0684* (2013.01);
(Continued)

(58) Field of Classification Search
CPC ....... A61B 1/06; A61B 1/0646; A61B 1/0661; A61B 1/0653; G02B 23/2461; G02B 23/243; G02B 23/2415
See application file for complete search history.

(56) References Cited

U.S. PATENT DOCUMENTS 6,034,407 A *  3/2000  Tennant ............ H01L 27/14652
                                                          257/440
9,766,447 B2 *  9/2017  Sakai ................... A61B 1/0638
(Continued)

FOREIGN PATENT DOCUMENTS

CN    203258507 U    10/2013
CN    103619234 A     3/2014
(Continued)

OTHER PUBLICATIONS

Chinese Office Action dated Oct. 30, 2017 issued in counterpart Chinese Application No. 201580043200.8.
(Continued)

*Primary Examiner* — Andrew Yang
(74) *Attorney, Agent, or Firm* — Holtz, Holtz & Volek PC

(57) ABSTRACT

A light-source device includes: two long-wavelength light sources that emit red long-wavelength light beams (LWLs); a broadband light source that emits a green broadband light beam (BL); and a multiplexing portion that multiplexes a wavelength region greater than a first predetermined wavelength $\lambda 1$ of one of the LWLs having a longer peak wavelength and a wavelength region equal to or less than $\lambda 1$ of the other LWL having a shorter peak wavelength, and that multiplexes a wavelength region greater than a second predetermined wavelength $\lambda 2$ of the other LWL and a wavelength region equal to or less than $\lambda 2$ of the BL, wherein intensities of the LWLs at $\lambda 1$ are equal to or greater than 10% of the peak intensities thereof and intensities of the other LWL and the BL at $\lambda 2$ are equal to or greater than 10% of the peak intensities thereof.

4 Claims, 12 Drawing Sheets

(52) U.S. Cl.
CPC ..... *G02B 6/29388* (2013.01); *G02B 23/2469* (2013.01); *A61B 1/0653* (2013.01)

(56) References Cited

U.S. PATENT DOCUMENTS

| | | | |
|---|---|---|---|
| 10,085,611 B2* | 10/2018 | Yabe | ............. A61B 1/0638 |
| 2004/0263500 A1 | 12/2004 | Sakata | |
| 2007/0070304 A1 | 3/2007 | Sakata | |
| 2007/0070305 A1 | 3/2007 | Sakata | |
| 2009/0206322 A1 | 8/2009 | Brandes | |
| 2011/0303896 A1 | 12/2011 | Brandes | |
| 2013/0188331 A1 | 7/2013 | Jaffe et al. | |
| 2013/0188383 A1 | 7/2013 | Jaffe et al. | |
| 2013/0188384 A1 | 7/2013 | Jaffe et al. | |
| 2013/0188388 A1 | 7/2013 | Jaffe et al. | |
| 2014/0054450 A1 | 2/2014 | Shirota et al. | |
| 2014/0293651 A1 | 10/2014 | Ito et al. | |
| 2016/0037999 A1 | 2/2016 | Yusuke et al. | |
| 2016/0306163 A1 | 10/2016 | Sakai et al. | |

FOREIGN PATENT DOCUMENTS

| | | |
|---|---|---|
| EP | 2702928 A1 | 3/2014 |
| EP | 2976989 A1 | 1/2016 |
| EP | 3132738 A1 | 2/2017 |
| JP | 2001042431 A | 2/2001 |
| JP | 2004151173 A | 5/2004 |
| JP | 2005157221 A | 6/2005 |
| JP | 2005173625 A | 6/2005 |
| JP | 2011512671 A | 4/2011 |
| JP | 2013125608 A | 6/2013 |
| JP | 2015231553 A | 12/2015 |
| WO | 2009102485 A1 | 8/2009 |

OTHER PUBLICATIONS

International Search Report (ISR) and Written Opinion dated Nov. 2, 2015 issued in International Application No. PCT/JP2015/072634.
Extended European Search Report (EESR) dated Apr. 6, 2018 issued in counterpart European Application No. 15833082.9.

* cited by examiner

LIGHT-SOURCE DEVICE

CROSS-REFERENCE TO RELATED APPLICATIONS

This is a continuation of International Application PCT/JP2015/072634, with an international filing date of Aug. 10, 2015, which is hereby incorporated by reference herein in its entirety. This application claims the benefit of Japanese Patent Application No. 2014-169408 filed on Aug. 22, 2014, the content of which is incorporated herein by reference.

TECHNICAL FIELD

The present invention relates to a light-source device.

BACKGROUND ART

In the related art, there is a known light-source device that uses a plurality of solid-state light sources such as LEDs (light emitting diodes) that emit monochromatic light beams and that generate a white illumination light beam by multiplexing red, green, and blue monochromatic light beams (for example, see Patent Literatures 1 to 3).

The green light beam emitted by the green LED has a lower light level as compared with the red light beam and the blue light beam emitted by the red LED and the blue LED, respectively, and, furthermore, the peak wavelength thereof is skewed toward the short-wavelength side of the green wavelength region. Therefore, in the spectrum of the generated illumination light beam, a truncated wavelength region is created between the peak wavelength of the green light beam and the peak wavelength of the red light beam, and thus, it is not possible to generate an illumination light beam having an ideal color temperature. Therefore, in Patent Literature 3, a white LED is used in addition to the red, green, and blue LEDs, and the color temperature of the illumination light beam is adjusted by correcting the spectrum of the green wavelength region by using a certain component of the white light beam emitted by the white LED.

In particular, in the case of a light-source device that is applied to a medical endoscope, in order to accurately observe and diagnose mucosa on the surface of an internal organ, which serves as an observation subject, by using an endoscope video image, the spectral characteristics of the green-to-red wavelength region are important. In other words, although the mucosa exhibits relatively high spectral reflectance in the green-to-red wavelength region, the spectral reflectance is not constant. Therefore, in order to accurately reproduce the tint of the mucosa in an endoscope video image, it is necessary to illuminate the mucosa with an illumination light beam having a good spectral characteristics with a low level spectral truncation in the green-to-red wavelength region.

CITATION LIST

Patent Literature

{PTL 1} Japanese Unexamined Patent Application, Publication No. 2005-173625
{PTL 2} Japanese Unexamined Patent Application, Publication No. 2005-157221
{PTL 3} Japanese Unexamined Patent Application, Publication No. 2004-151173

SUMMARY OF INVENTION

The present invention provides a light-source device including: at least two long-wavelength light sources that individually emit long-wavelength light beams that have peak wavelengths, which are different from each other, in a red wavelength region; a single broadband light source that emits a broadband light beam that includes a green wavelength region from 500 nm to 580 nm, that has a peak wavelength in a region that is equal to or less than 580 nm, and that has, on a long-wavelength side, a wavelength region that overlaps with a wavelength region of the long-wavelength light beam on a short-wavelength side; and a multiplexing portion that multiplexes a wavelength region, which is greater than a first predetermined wavelength in the red wavelength region, of one of the long-wavelength light beams having a peak wavelength on a longer-wavelength side, and a wavelength region, which is equal to or less than the first predetermined wavelength, of the other long-wavelength light beam having a peak wavelength on a shorter-wavelength side, and that multiplexes a wavelength region of the other long-wavelength light beam that is greater than a second predetermined wavelength and a wavelength region of the broadband light beam that is equal to or less than the second predetermined wavelength, wherein the first predetermined wavelength is a wavelength at which an intensity of the one of the long-wavelength light beams is equal to or greater than 10% of the peak intensity thereof and at which an intensity of the other long-wavelength light beam is equal to or greater than 10% of the peak intensity thereof, and wherein the second predetermined wavelength is a wavelength between the peak wavelength of the other long-wavelength light beam and the peak wavelength of the broadband light beam, and is a wavelength at which an intensity of the other long-wavelength light beam is equal to or greater than 10% of the peak intensity thereof, and at which an intensity of the broadband light beam is equal to or greater than 10% of the peak intensity thereof.

DESCRIPTION OF EMBODIMENT

A light-source device 1 according to an embodiment of the present invention will be described below with reference to the drawings.

Figure 1:
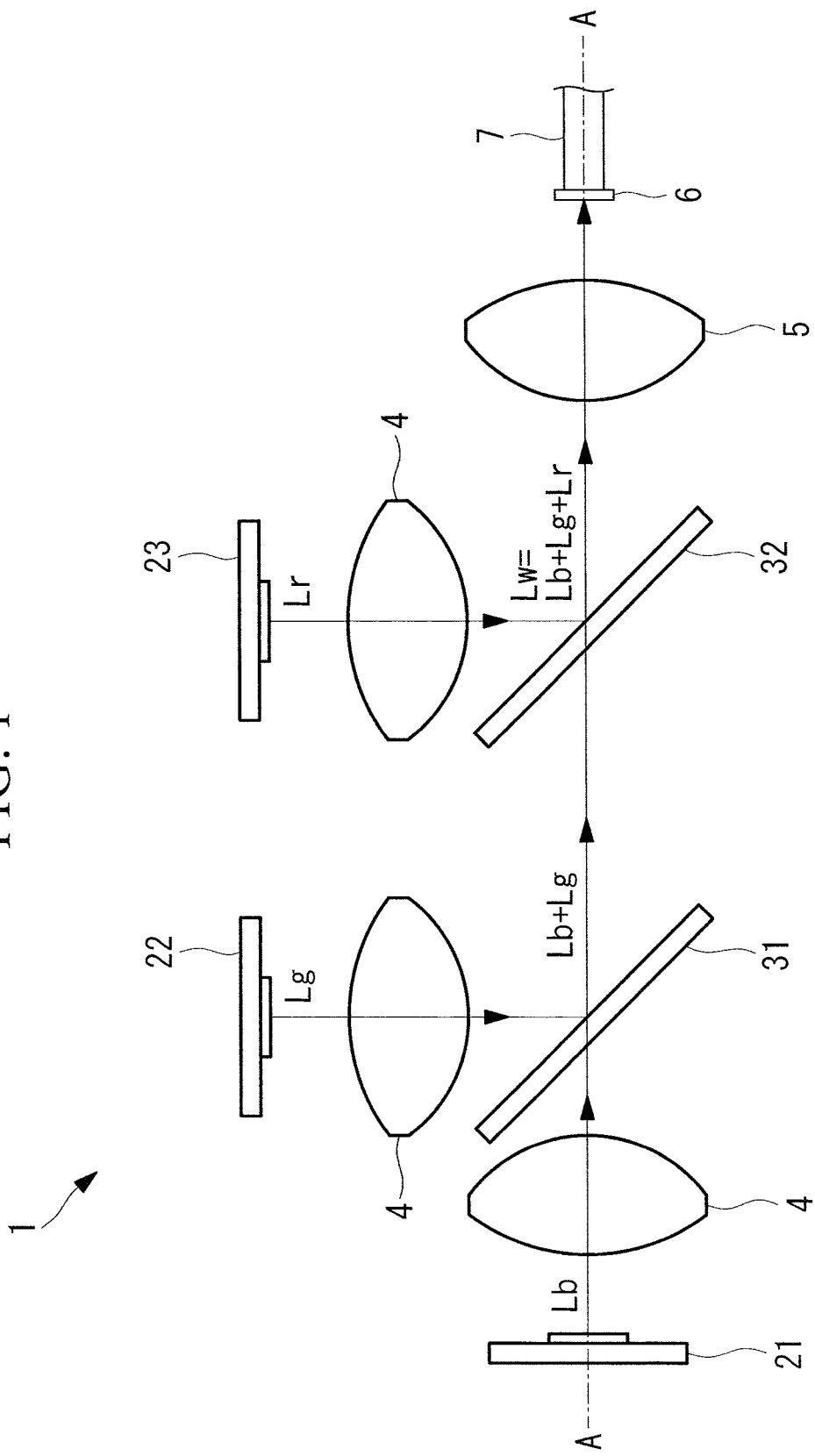
FIG. 1 is an overall configuration diagram of a light-source device according to an embodiment of the present invention.

As shown in FIG. 1, the light-source device 1 according to this embodiment is provided with: three LEDs 21, 22, and 23; two dichroic filters 31 and 32 that generate a white illumination light beam Lw by multiplexing three light beams Lb, Lg, and Lr emitted from the LEDs 21, 22, and 23; three collimator lenses 4 that are disposed at immediately subsequent stages of the individual LEDs 21, 22, and 23; and a converging lens 5 that makes the illumination light beam Lw generated by the dichroic filters (multiplexing portions) 31 and 32 converge.

Figure 2:
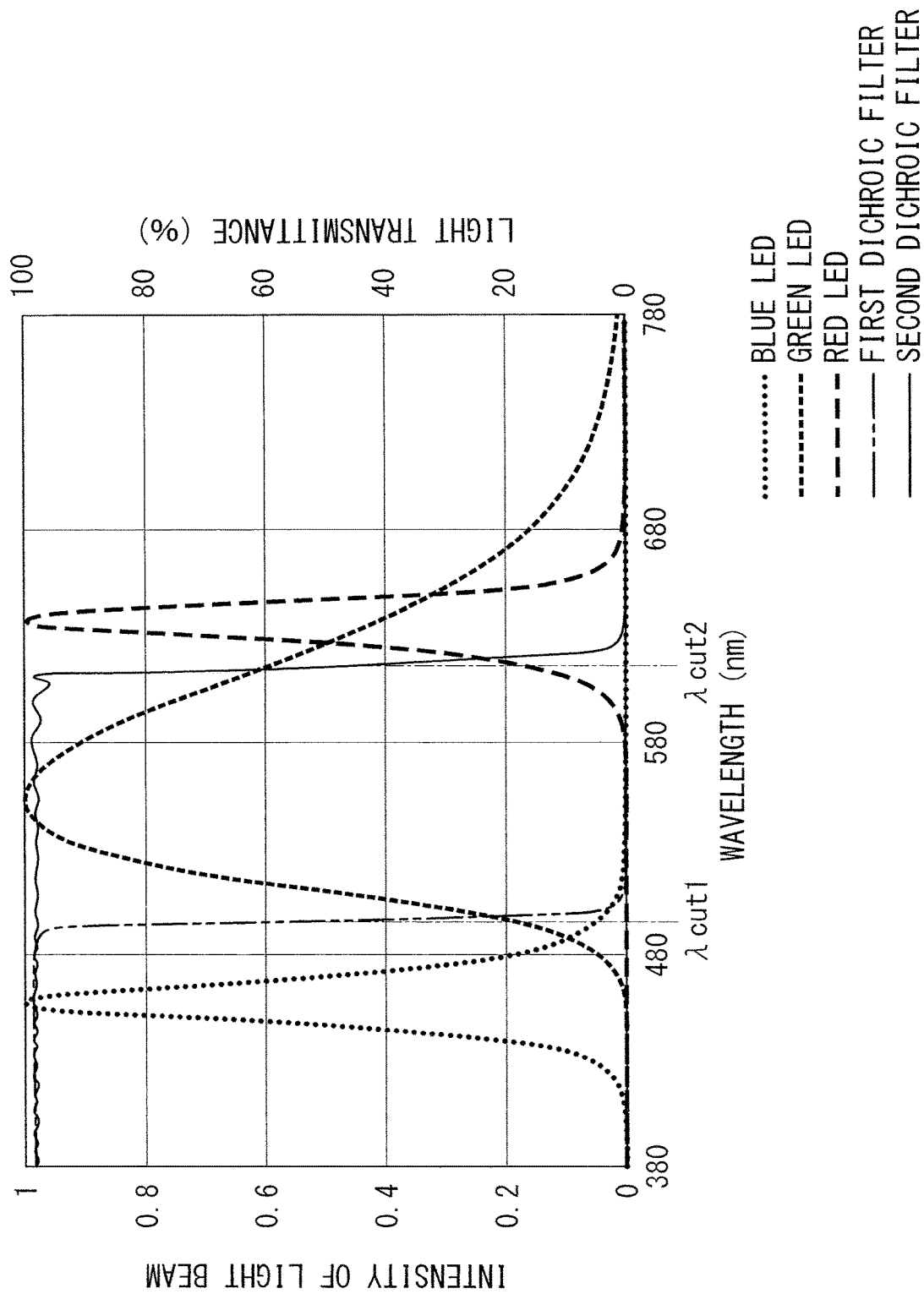
FIG. 2 is a graph showing emission spectra (left axis) of blue, green, and red LEDs provided in the light-source device in FIG. 1 and spectral transmittances (right axis) of first and second dichroic filters.

FIG. 2 shows the spectra of the light beams Lb, Lg, and Lr emitted by the LEDs 21, 22, and 23 and the light transmission characteristics of the dichroic filters 31 and 32. In FIG. 2, the intensities of the light beams Lb, Lg, and Lr are normalized by assuming that maximum values of the respective intensities are 1.

The LEDs 21, 22, and 23 are a single blue LED (short-wavelength light source) 21 that emits a blue light beam (short-wavelength light beam) Lb, a single green LED (broadband light source) 22 that emits a green light beam (broadband) Lg, and a single red LED (long-wavelength light source) 23 that emits a red light beam (long-wavelength light beam) Lr.

The blue light beam Lb is a narrowband light beam formed of a spectrum in which the half width is approximately 20 nm to 30 nm, and has a peak wavelength at approximately 460 nm.

The red light beam Lr is a narrowband light beam formed of a spectrum in which the half width is approximately 20 nm to 30 nm, and has a peak wavelength at approximately 630 nm.

The green light beam Lg is a broadband light beam formed of a spectrum in which the half width is approximately 100 nm or greater, and has a peak wavelength at approximately 550 nm. In other words, the spectrum of the green light beam Lg is also in the red wavelength region, and the wavelength region of the green light beam Lg on the long-wavelength side overlaps at least with the wavelength region of the red light beam Lr on the short-wavelength side.

The green LED 22 is disposed so that an emission optical axis thereof intersects an emission optical axis A of the blue LED 21. The red LED 23 is disposed so that an emission optical axis thereof intersects the emission optical axis A of the blue LED 21 at a position farther away from the blue LED 21 than the green LED 22 is.

The first dichroic filter 31 is a short pass filter that has a cut-off wavelength (predetermined wavelength) $\lambda\text{cut1}$ at approximately 500 nm, that allows light having a wavelength that is equal to or less than the cut-off wavelength $\lambda\text{cut1}$ to pass therethrough, and that reflects light having a wavelength that is greater than the cut-off wavelength $\lambda\text{cut1}$.

The second dichroic filter 32 is a short pass filter that has a cut-off wavelength $\lambda\text{cut2}$ between the peak wavelength of the green light beam Lg and the peak wavelength of the red light beam Lr, that allows light having a wavelength that is equal to or less than the cut-off wavelength $\lambda\text{cut2}$ to pass therethrough, and that reflects light having a wavelength that is greater than the cut-off wavelength $\lambda\text{cut2}$.

The first dichroic filter 31 is disposed at a position at which the emission optical axis A of the blue LED 21 and the emission optical axis of the green LED 22 intersect each other. With the first dichroic filter 31, the entirety of the blue light beam Lb emitted from the blue LED 21 is allowed to pass therethrough along the output optical axis A, whereas most of the green light beam Lg emitted from the green LED 22 is reflected along the output optical axis A.

The second dichroic filter 32 is disposed at a position at which the emission optical axis A of the blue LED 21 and the emission optical axis of the red LED 23 intersect each other. With the second dichroic filter 32, the entirety of the blue light beam Lb is allowed to pass therethrough along the output optical axis A, whereas, of the green light beam Lg reflected by the first dichroic filter 31, light in a wavelength region that is greater than the cut-off wavelength $\lambda\text{cut2}$ is reflected, and light in a wavelength region that is equal to or less than the cut-off wavelength $\lambda\text{cut2}$ is allowed to pass therethrough along the output optical axis A. Furthermore, with the second dichroic filter 32, of the red light beam Lr emitted from the red LED 23, light in a wavelength region that is greater than the cut-off wavelength $\lambda\text{cut2}$ is reflected along the output optical axis A, and light in a wavelength region that is equal to or less than the cut-off wavelength $\lambda\text{cut2}$ is allowed to pass therethrough.

As has been described above, the blue, green, and red light beams Lb, Lg, and Lr are multiplexed in the subsequent stage of the second dichroic filter 32, thus generating the white illumination light beam Lw. The generated illumination light beam Lw is made to converge at a cover glass 6 on the optical axis A by means of the converging lens 5, and thus, the illumination light beam Lw is output from the cover glass 6 to outside the light-source device 1.

Here, the cut-off wavelength $\lambda\text{cut2}$ of the second dichroic filter 32 is set to be a wavelength at which the intensity of the green light beam Lg at that cut-off wavelength $\lambda\text{cut2}$ is equal to or greater than 10% of the peak intensity of the green light beam Lg and at which the intensity of the red light beam Lr at that cut-off wavelength $\lambda\text{cut2}$ is equal to or greater than 10% of the peak intensity of the red light beam Lr. In the example shown in FIG. 2, the cut-off wavelength $\lambda\text{cut2}$ is set to be approximately 615 nm.

In the case in which intensities of the individual light beams Lr and Lg at the cut-off wavelength $\lambda\text{cut2}$ are less than 10% of the respective peak intensities, wavelength regions in which intensities are insufficient could occur at the cut-off wavelength $\lambda\text{cut2}$ of the illumination light beam Lw and in the vicinity thereof. As a result, it is difficult to ensure a good color reproduction for the illumination light beam Lw, described later.

The individual collimator lenses 4 are convex lenses whose focal points are placed at light emitting portions of the individual LEDs 21, 22, and 23, individually receive the light beams Lb, Lg, and Lr that are emitted from the light emitting portions of the LEDs 21, 22, and 23 in the form of diverging light bundles, and individually emit the light bundles toward the dichroic filters 31 and 32 following conversion to parallel light bundles having substantially the same light-bundle diameters. In this way, the blue light beam Lb, the green light beam Lg, and the red light beam Lr are combined, thus generating the illumination light beam Lw.

Next, the operation of the thus-configured light-source device 1 will be described in terms of an example in which the light-source device 1 is used as a light-source device for a medical endoscope with which the interior of a living organism is observed. Reference sign 7 indicates an illumination light guide of an endoscope connected to the light-source device 1.

The three-color light beams Lb, Lg, and Lr emitted from the individual LEDs 21, 22, and 23 are multiplexed by the two dichroic filters 31 and 32 on the same emission optical axis A, and thus, the white illumination light beam Lw is generated in the subsequent stage of the second dichroic filter 32. The generated illumination light beam Lw is made to converge by means of the converging lens 5, and is made to enter the light guide 7.

The illumination light beam Lw that has entered the light guide 7 is guided by the light guide 7 to the distal end of the light guide 7 disposed at the distal end of the endoscope, and is radiated toward an observation subject from the distal end of the endoscope. Reflected light of the illumination light beam Lw coming from the observation subject is received by an image-acquisition element such as a CCD image sensor built into the distal end of the endoscope, thus forming a color image.

Figure 3:
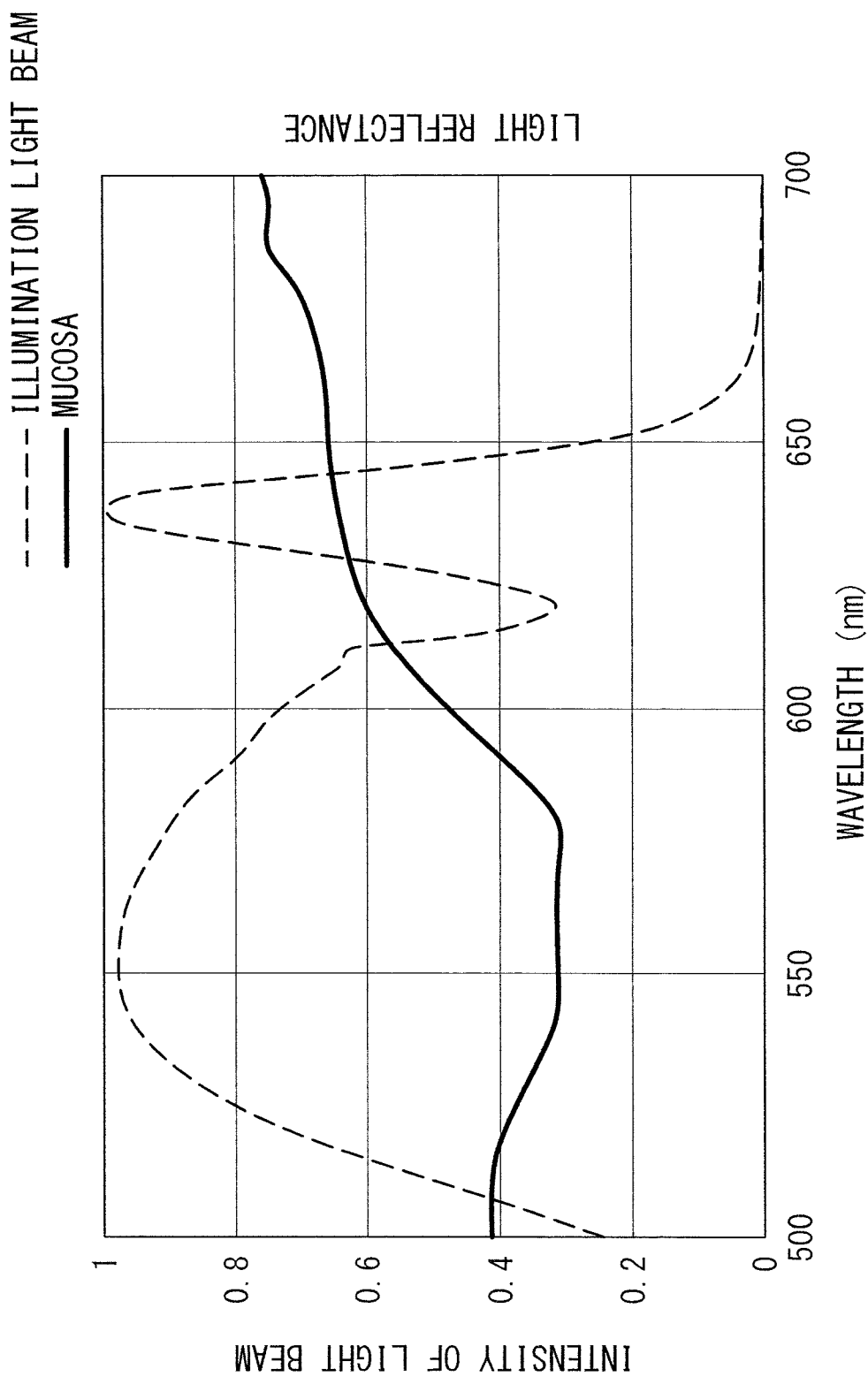
FIG. 3 is a graph showing the spectrum (left axis) of an illumination light beam generated by the light-source device in FIG. 1 and the spectral reflectance (right axis) of mucosa.

Here, the spectral reflectance of mucosa exhibits a large change in a wavelength region from 500 nm to 650 nm, as shown in FIG. 3. In FIG. 3, the intensity of the illumination light beam Lw is normalized by assuming that the maximum value is 1.

Figure 10:
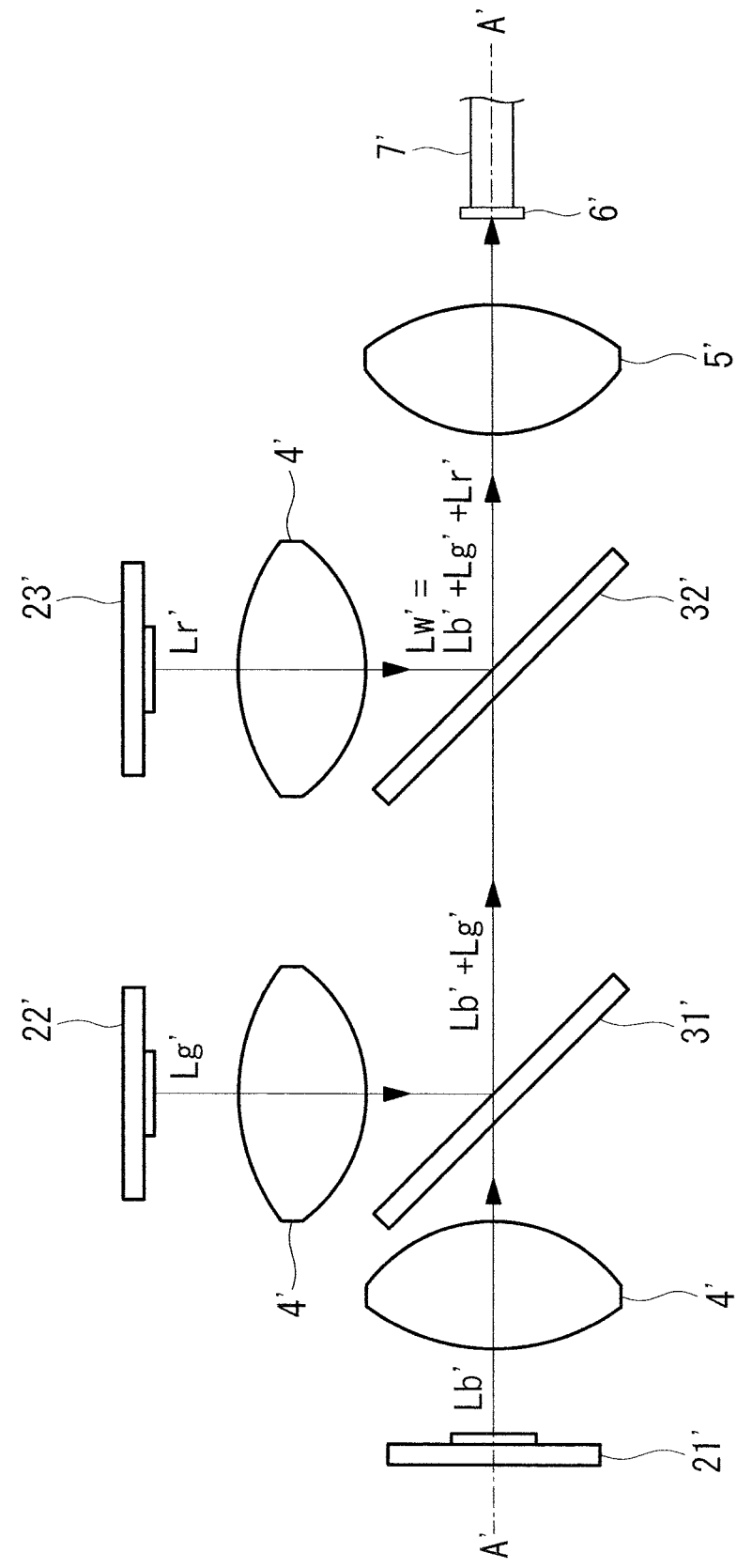
FIG. 10 is an overall configuration diagram showing a conventional light-source device.

Here, a conventional light-source device 1' will be described with reference to FIGS. 10 to 12. As shown in FIG. 10, the basic configuration of the light-source device 1' is substantially the same as that of the light-source device 1 according to this embodiment, a blue LED 21', a red LED 23', a first dichroic filter 31', collimator lenses 4', and a converging lens 5' are configured in the same way as the blue LED 21, the red LED 23, the first dichroic filter 31, the collimator lenses 4, and the converging lens 5, respectively. However, as shown in FIG. 11, the optical characteristics of the green LED 22' and the second dichroic filter 32' in the conventional light-source device 1' are different from the optical characteristics of the green LED 22 and the second dichroic filter 32, respectively.

Figure 11:
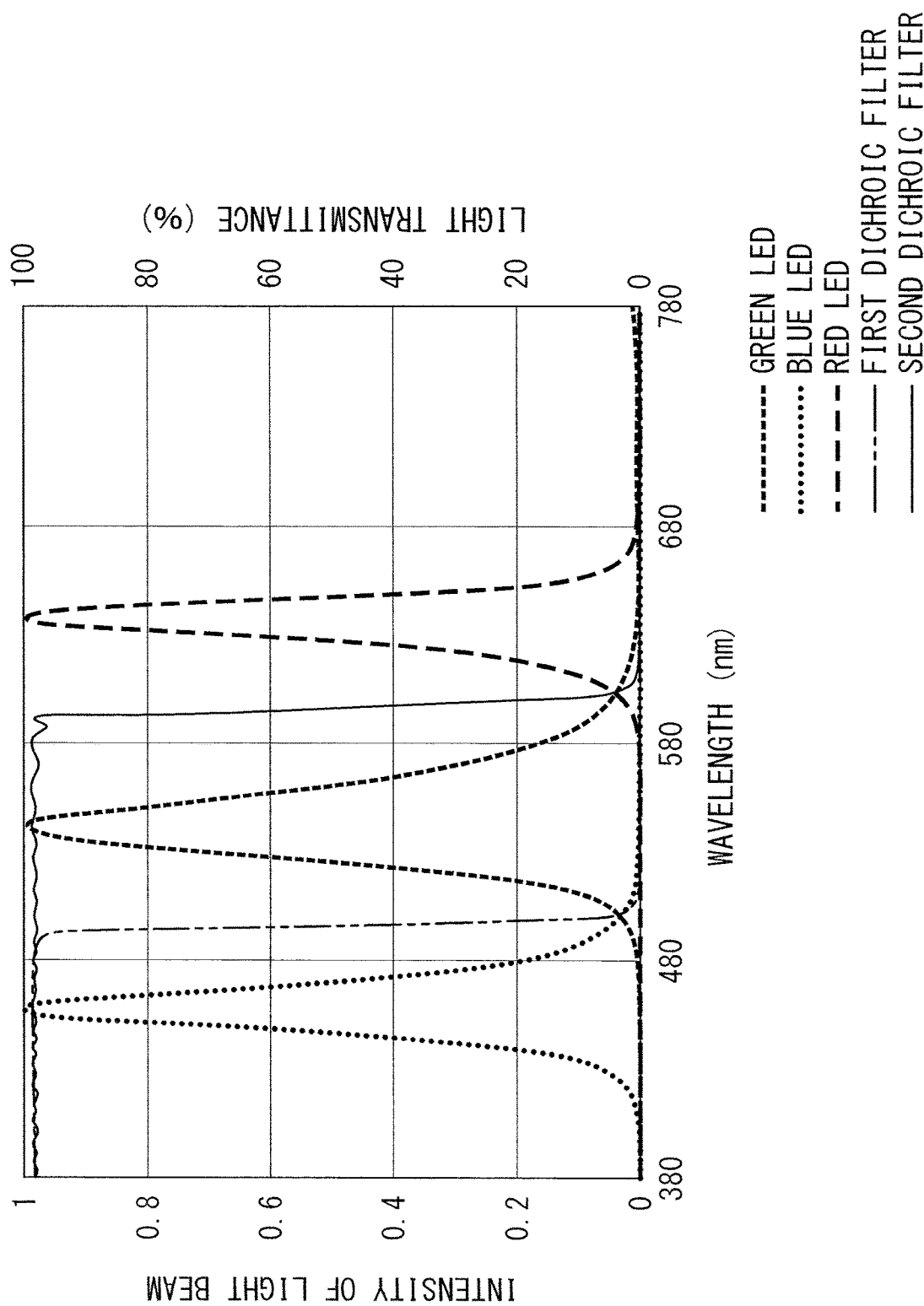
FIG. 11 is a graph showing the emission spectra (left axis) of blue, green, and red LEDs provided in the light-source device in FIG. 10 and the spectral transmittances (right axis) of first and second dichroic filters.
Figure 12:
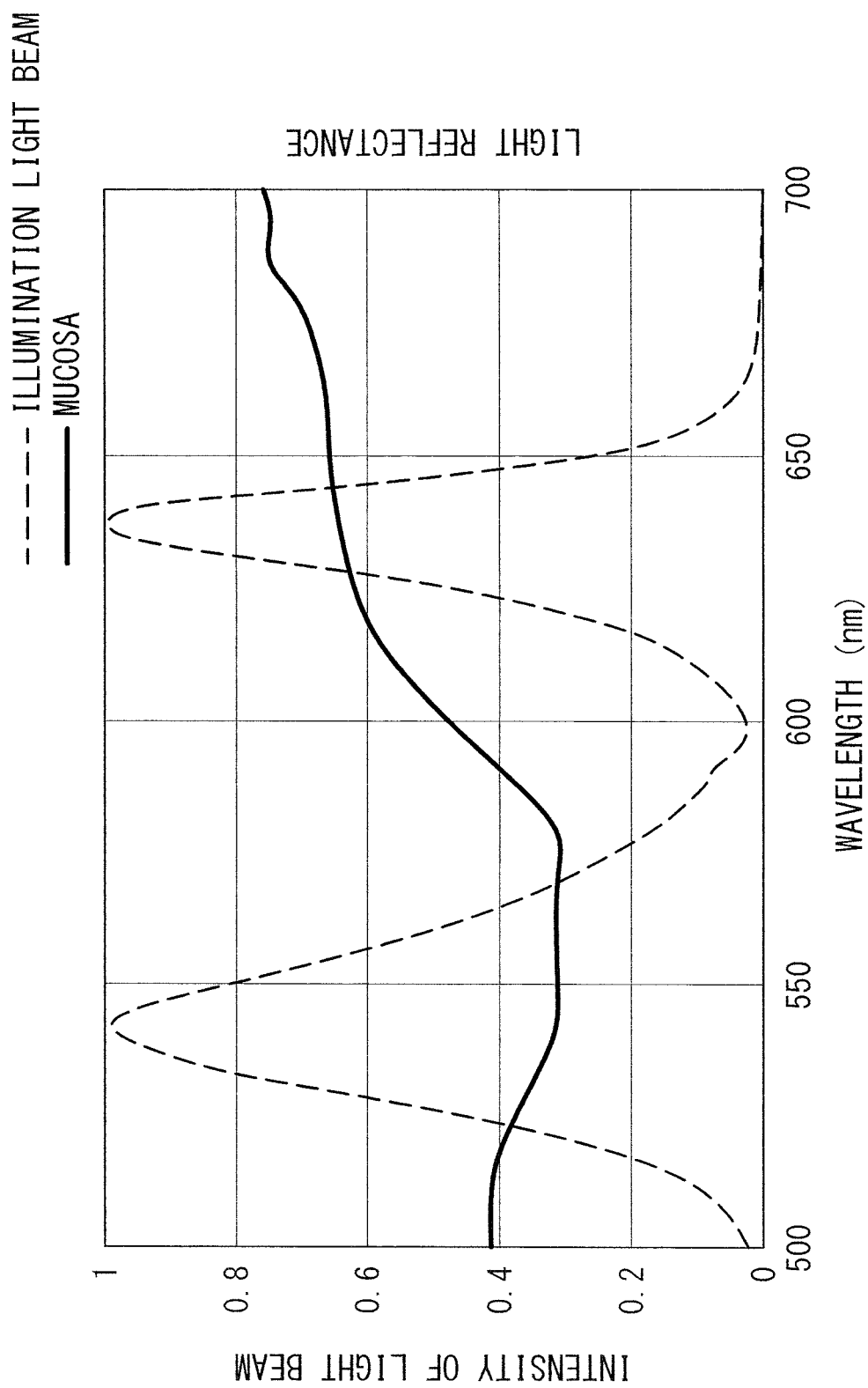
FIG. 12 is a graph showing the spectrum (left axis) of an illumination light beam generated by the light-source device in FIG. 10 and the spectral reflectance (right axis) of mucosa.

As shown in FIGS. 10 and 11, in the case of the conventional light-source device 1' in which an LED that emits a narrowband green light beam Lg' is used as the green LED 22', the spectrum of a generated illumination light beam Lw' has, as shown in FIG. 12, a wavelength truncation in a green-to-red wavelength region in which the spectral reflectance of the mucosa exhibits a large change. This means that it is not possible to accurately reproduce the color of the mucosa when the illumination light beam Lw' is radiated onto the mucosa.

With this embodiment, the illumination light beam Lw that is generated by multiplexing the broadband green light beam Lg and the red light beam Lr has a continuous spectrum over the entire wavelength region from 500 nm to 650 nm with a low level of wavelength truncation. Furthermore, the cut-off wavelength λcut2 of the second dichroic filter 32 that multiplexes the green light beam Lg and the red light beam Lr is set to be a wavelength at which both of the light beams Lg and Lr have intensities that are equal to or greater than 10% of the peak intensities of the light beams Lg and Lr. By doing so, as shown in FIG. 3, the illumination light beam Lw has a high enough intensity at the cut-off wavelength λcut2, at which the intensity thereof becomes relatively low in a wavelength region from 500 nm to 650 nm, and in the vicinity thereof, and thus, the illumination light beam Lw has good spectral characteristics over the entire wavelength region from 500 nm to 650 nm with a low level of wavelength truncation.

Such an illumination light beam Lw is advantageous for reproducing a subtle difference possessed by the mucosa with respect to the tint between green and red. With an endoscope color image obtained by capturing an image of the mucosa illuminated with the illumination light beam Lw having particularly excellent color rendering properties for colors from green to red, as has been described, there is an advantage in that it is possible to accurately reproduce the subtle tint of the mucosa.

Although the three color LEDs 21, 22, and 23 are provided in this embodiment, it is possible to increase the number of colors of the LEDs, as appropriate.

Figure 4:
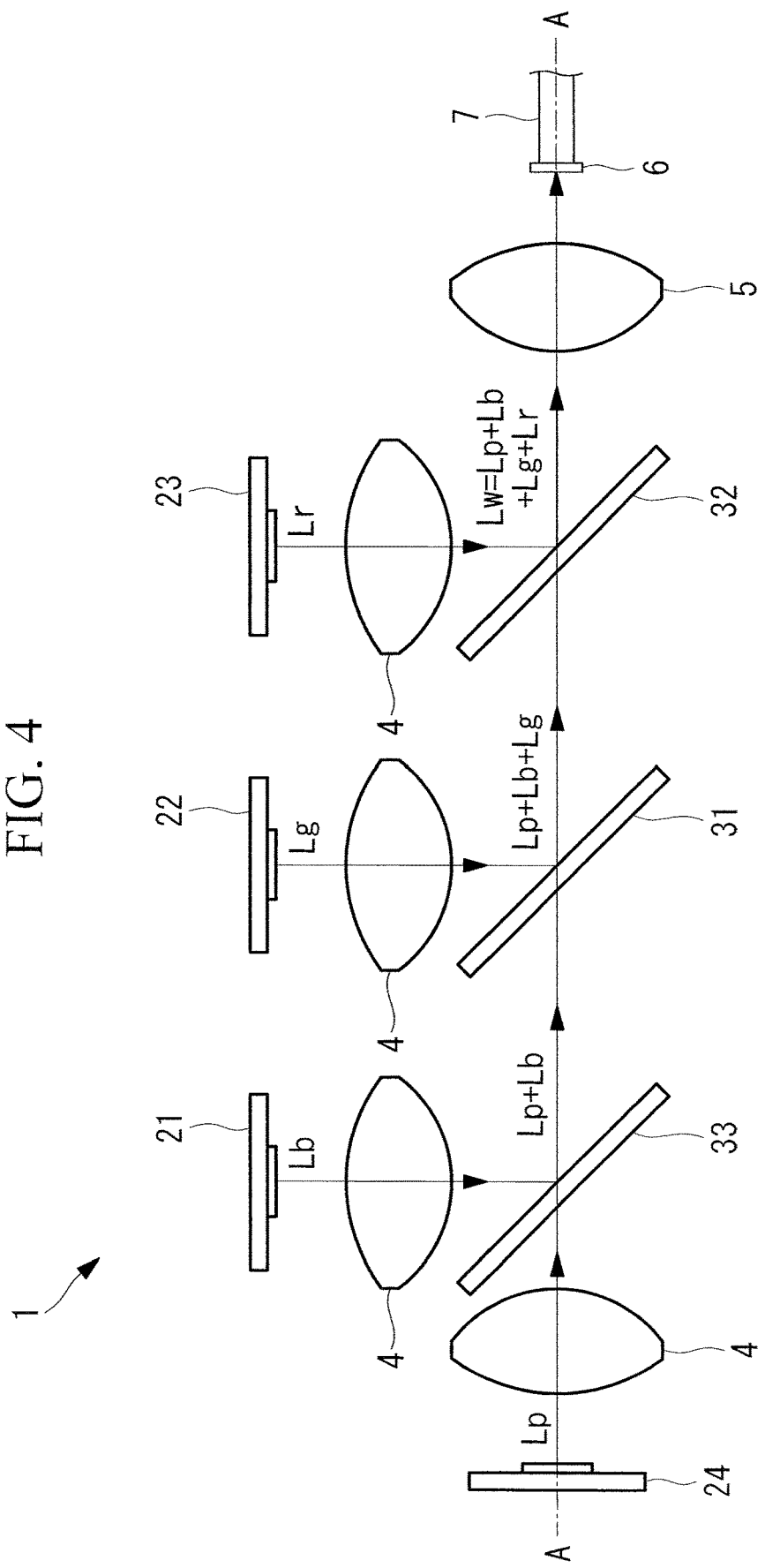
FIG. 4 is an overall configuration diagram showing a modification of the light-source device in FIG. 1.

FIG. 4 shows a configuration that is additionally provided with a purple LED (short-wavelength light source) 24 that emits a narrowband purple light beam (short-wavelength light beam) Lp that has a single peak wavelength approximately from 410 to 420 nm, and a third dichroic filter 33 that multiplexes the purple light beam Lp and the blue light beam Lb on the emission optical axis A.

Figure 5:
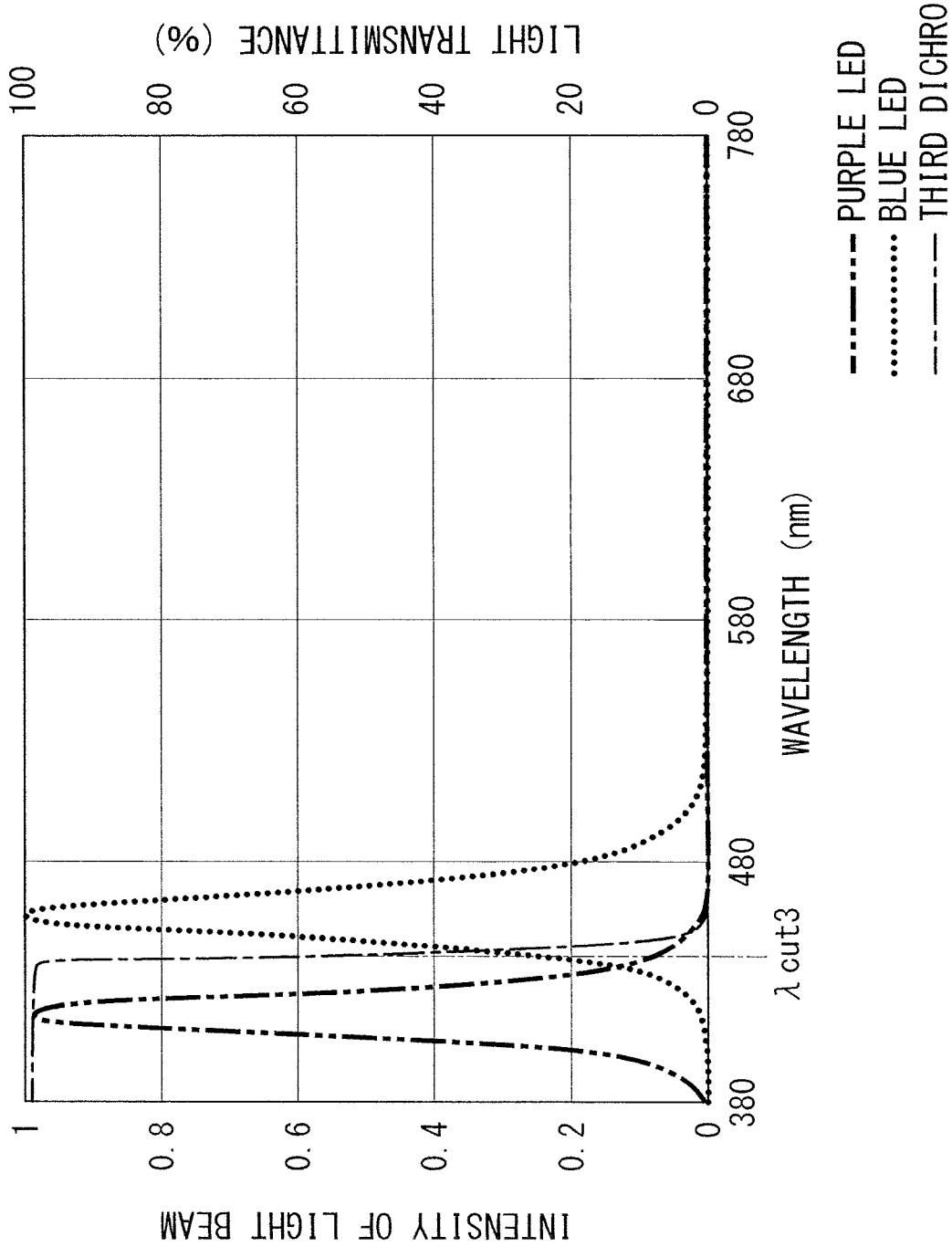
FIG. 5 is a graph showing the emission spectra (left axis) of blue and purple LEDs provided in the light-source device in FIG. 4 and the spectral transmittance (right axis) of a third dichroic filter.

As shown in FIG. 5, the third dichroic filter 33 is a short pass filter that has a cut-off wavelength λcut3 between the peak wavelength of the blue light beam Lb and the peak wavelength of the purple light beam Lp. With the third dichroic filter 33, substantially the entirety of the purple light beam Lp is allowed to pass therethrough along the emission optical axis A, and most of the blue light beam Lb is reflected along the emission optical axis A. In this example, the cut-off wavelength λcut3 is set to be approximately 440 nm.

Here, a short wavelength region of the blue light beam Lb that is equal to or less than a predetermined wavelength (approximately 430 nm in examples shown in FIGS. 5 and 6) and a long wavelength region of the purple light beam Lp that is greater than the predetermined wavelength overlap with each other. The predetermined wavelength is set to be a wavelength at which the intensity of the blue light beam Lb is equal to or greater than 10% of the peak intensity thereof and the intensity of the purple light beam Lp is equal to or greater than 10% of the peak intensity thereof. By doing so, the illumination light beam Lw has spectral characteristics with a low level of wavelength truncation for all wavelengths in the blue wavelength region.

Figure 6:
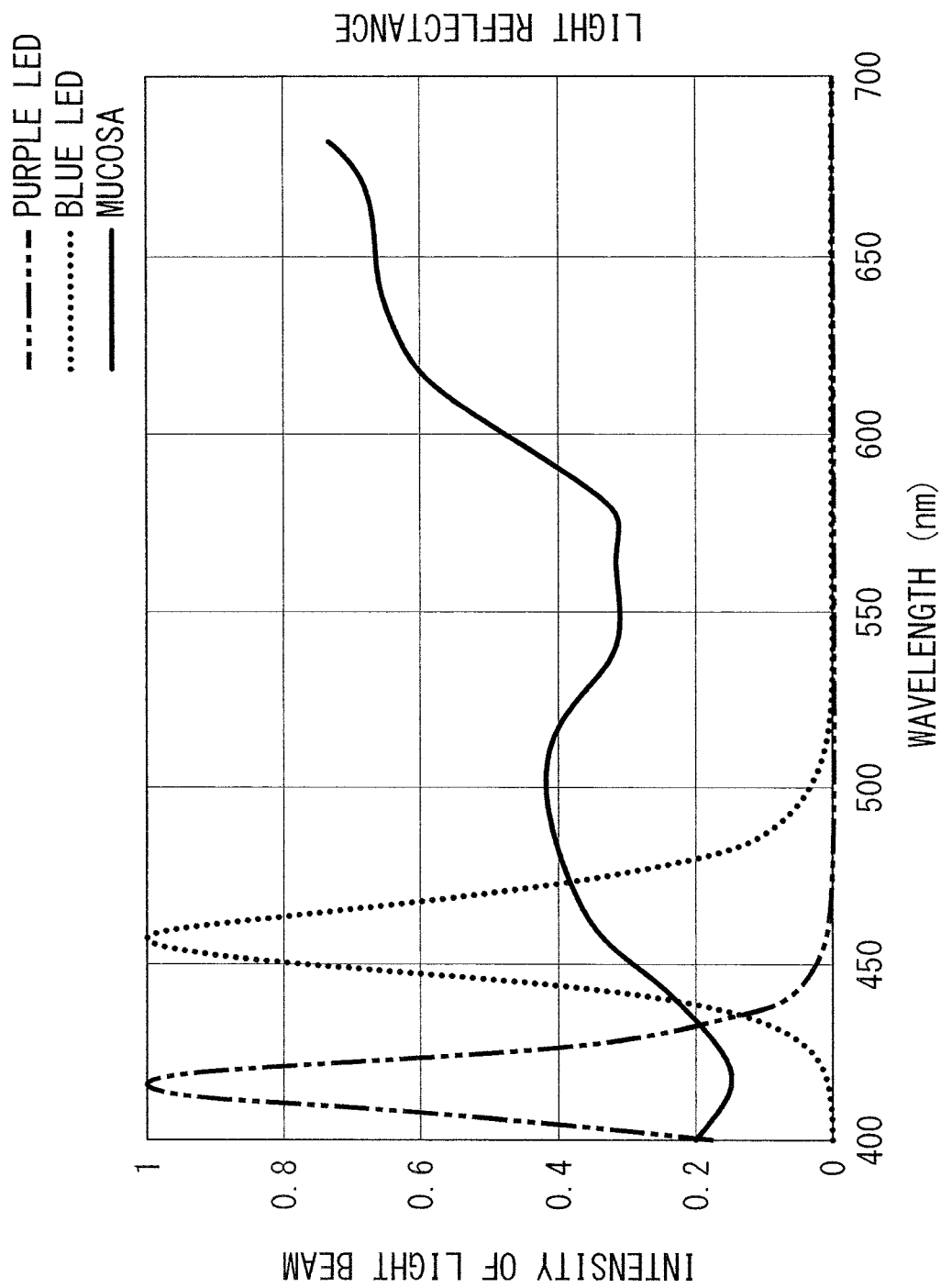
FIG. 6 is a graph showing the emission spectra (left axis) of the blue and purple LEDs provided in the light-source device in FIG. 4 and the spectral reflectance (right axis) of the mucosa.

As shown in FIG. 6, the spectral reflectance of the mucosa also differs in the blue wavelength region depending on the wavelength. Therefore, by using, in combination, the two LEDs 21 and 24 that have peak wavelengths in the blue wavelength region, good spectral characteristics with a low level of wavelength truncation are achieved also in the blue wavelength region of the illumination light beam Lw. In this way, by illuminating the mucosa with the illumination light beam Lw having excellent color rendering properties also in blue color, there is an advantage in that it is possible to accurately express a subtle difference in blue tint that the mucosa possesses.

Note that, in FIGS. 5 and 6, the intensities of the light beams Lb and Lp are normalized by assuming that the respective maximum values are 1.

Figure 7:
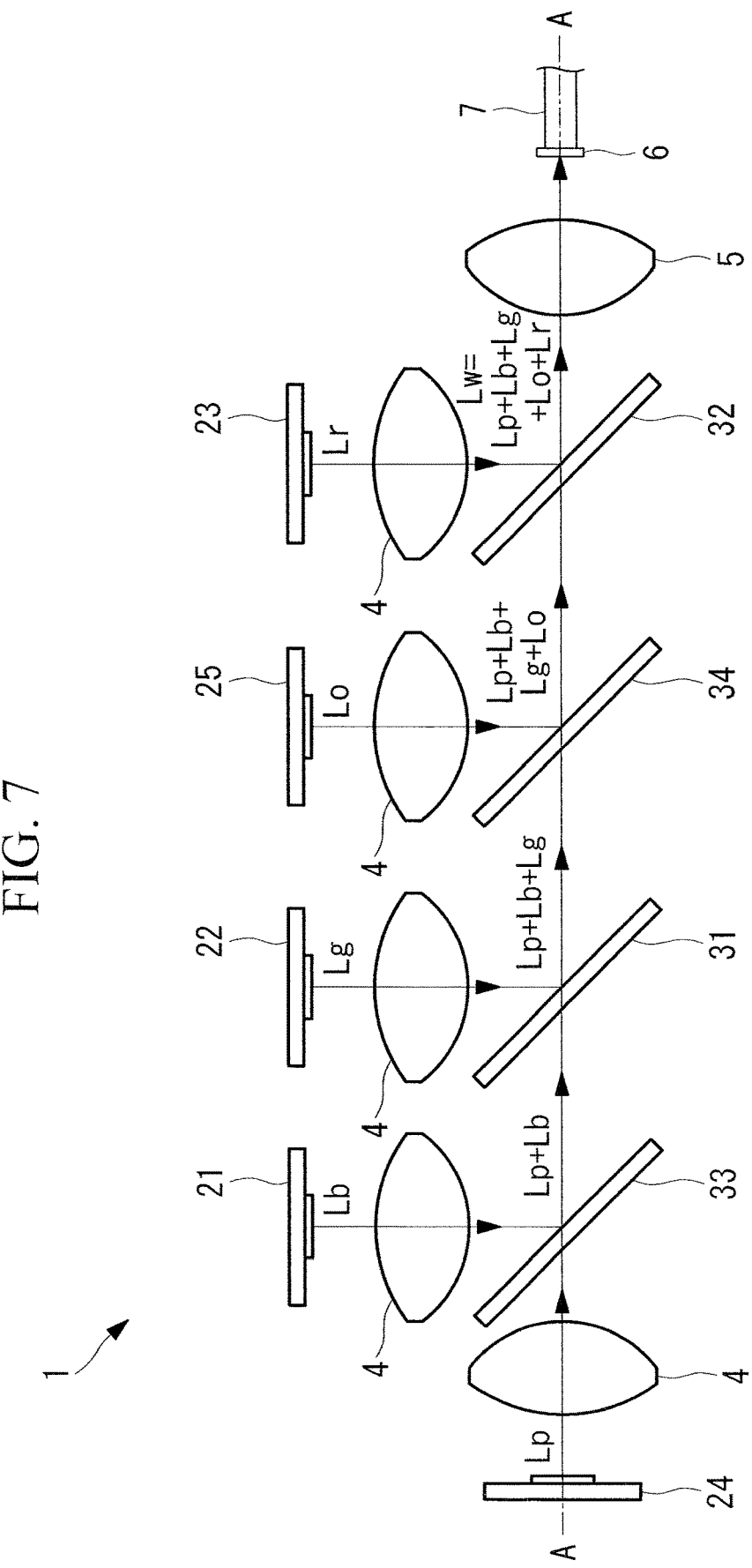
FIG. 7 is an overall configuration diagram showing another modification of the light-source device in FIG. 1.

FIG. 7 shows a configuration in which the configuration in FIG. 4 is additionally provided with an orange LED (long-wavelength light source) 25 that emits a narrowband orange light beam (long-wavelength light beam) Lo that has a peak wavelength at approximately 600 nm, and a fourth dichroic filter 34 that multiplexes the orange light beam Lo on the emission optical axis A. The fourth dichroic filter 34 is a short pass filter that has a cut-off wavelength between the peak wavelength of the green light beam Lg and the peak wavelength of the orange light beam Lo. The cut-off wavelength is set to be, for example, approximately 580 nm.

Figure 8:
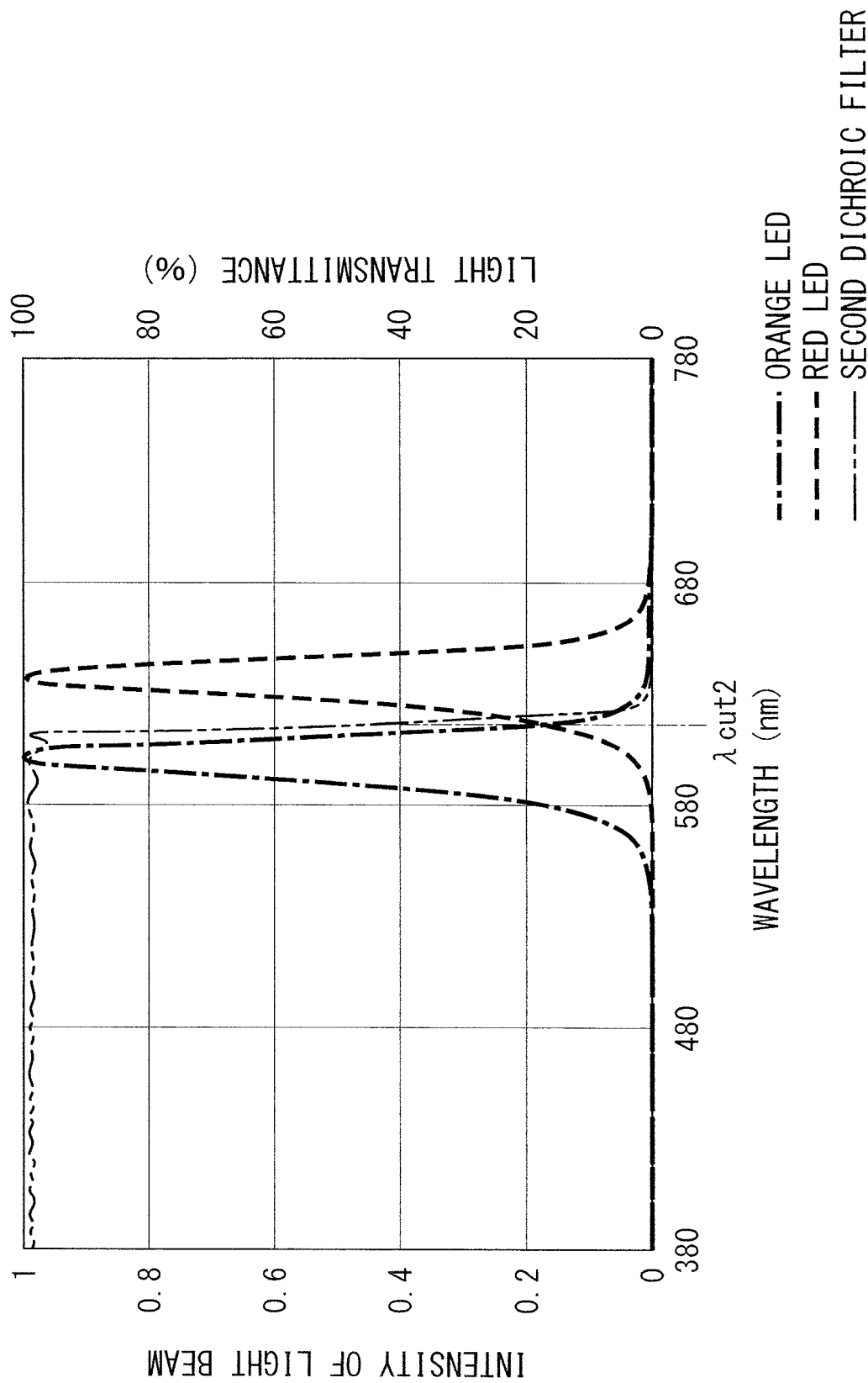
FIG. 8 is a graph showing emission spectra (left axis) of red and orange LEDs provided in the light-source device in FIG. 7 and the spectral transmittance (right axis) of a fourth dichroic filter.

As shown in FIG. 8, the cut-off wavelength (predetermined wavelength) λcut2 of the second dichroic filter 32 is positioned between the peak wavelength of the orange light beam Lo and the peak wavelength of the red light beam Lr. The intensity of the red light beam Lr at the cut-off wavelength λcut2 is equal to or greater than 10% of the peak intensity of the red light beam Lr, and the intensity of the orange light beam Lo at the cut-off wavelength λcut2 is equal to or greater than 10% of the peak intensity of the orange light beam Lo.

Figure 9:
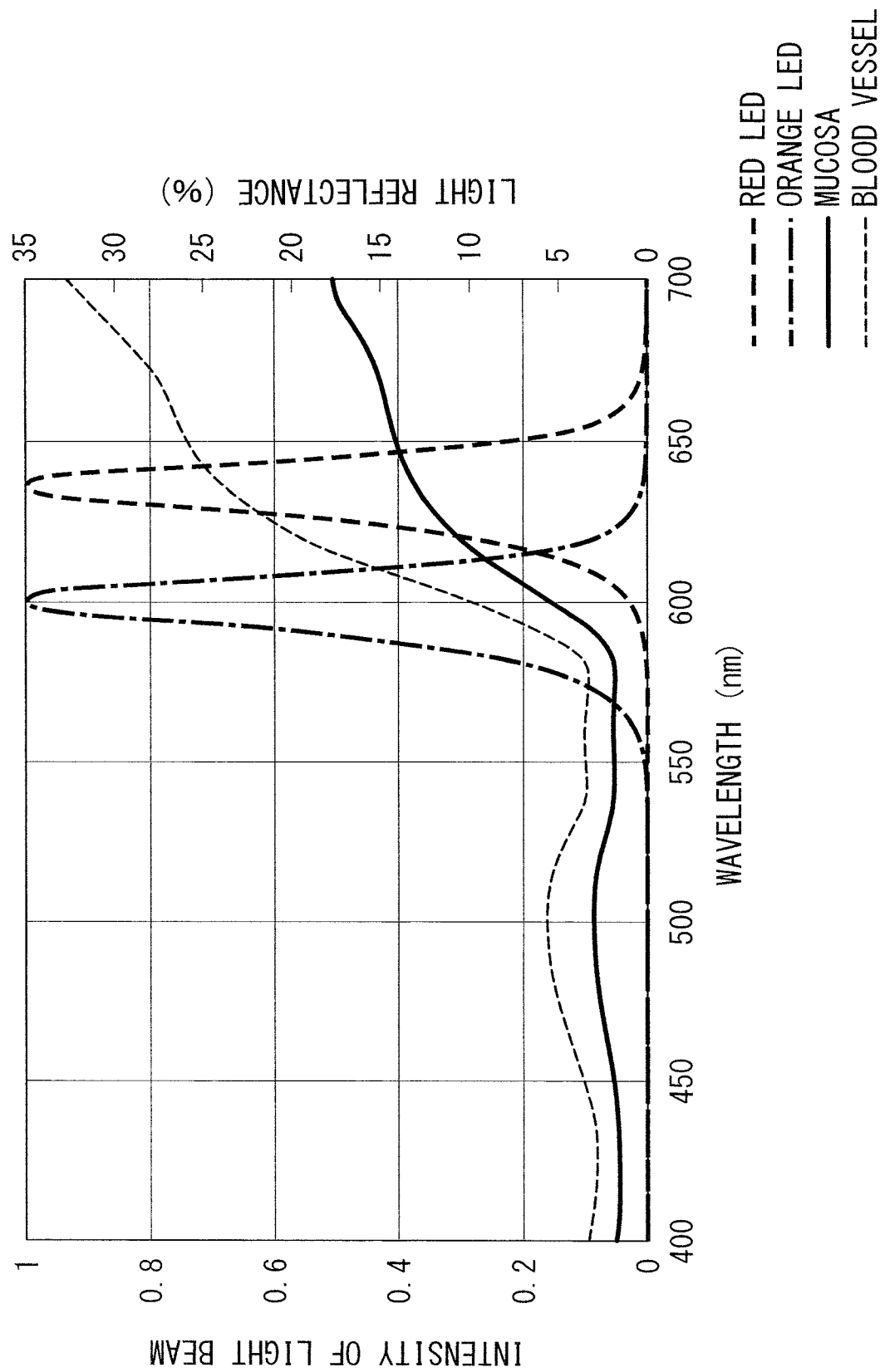
FIG. 9 is a graph showing the emission spectra (left axis) of the red and orange LEDs provided in the light-source device in FIG. 7 and the spectral reflectances (right axis) of mucosa and blood vessels.

As shown in FIG. 9, the spectral reflectances of the mucosa and blood vessels that are present in the mucosa differ in the red wavelength region depending on the wavelength. Therefore, by using, in combination, the two LEDs 23 and 25 that have peak wavelengths in the red wavelength region, good spectral characteristics with a low level of wavelength truncation are achieved also in the red wavelength region of the illumination light beam Lw. In this was, by illuminating the mucosa with the illumination light beam Lw having excellent color rendering properties also in red color, there is an advantage in that it is possible to accurately express subtle differences in red tint between the mucosa and the blood vessels.

Note that, in FIGS. 8 and 9, the intensities of the light beams Lb and Lo are normalized by assuming that the respective maximum values are 1.

Furthermore, this embodiment may additionally be provided with an intensity-ratio adjusting portion that adjusts intensity ratios of the light beams Lb, Lg, Lr, Lp, and Lo to be multiplexed by the dichroic filters 31, 32, 33, and 34. The intensity-ratio adjusting portion is, for example, a power source (not shown) that supplies currents to the individual LEDs 21, 22, 23, 24, and 25, and, by separately adjusting the magnitudes of the currents to be supplied to the individual LEDs 21, 22, 23, 24, and 25, it is possible to adjust the intensity ratios of the light beams Lb, Lg, Lr, Lp, and Lo by adjusting the emission intensities of the individual LEDs 21, 22, 23, 24, and 25 independently of each other.

The image-acquisition element does not have the same detection sensitivities for light of all wavelengths, but has different detection sensitivities for each of the wavelengths. By adjusting the spectral characteristics of the illumination light beam Lw so as to be optimized for the spectral sensitivity characteristics of such an image-acquisition element, it is possible to ensure better color reproduction in an image acquired by using the image-acquisition element.

In addition, in this embodiment, although the green LED 22 that emits the broadband green light beam is employed as the broadband light source, alternatively, a light source that emits a white light beam, such as a white LED, may be employed.

From the above-described embodiment and modifications thereof, the following aspect of the invention is derived.

One aspect of the present invention is a light-source device including: at least two long-wavelength light sources that individually emit long-wavelength light beams that have peak wavelengths, which are different from each other, in a red wavelength region; a single broadband light source that emits a broadband light beam that includes a green wavelength region from 500 nm to 580 nm, that has a peak wavelength in a region that is equal to or less than 580 nm, and that has, on a long-wavelength side, a wavelength region that overlaps with a wavelength region of the long-wavelength light beam on a short-wavelength side; and a multiplexing portion that multiplexes a wavelength region, which is greater than a first predetermined wavelength in the red wavelength region, of one of the long-wavelength light beams having a peak wavelength on a longer-wavelength side, and a wavelength region, which is equal to or less than the first predetermined wavelength, of the other long-wavelength light beam having a peak wavelength on a shorter-wavelength side, and that multiplexes a wavelength region of the other long-wavelength light beam that is greater than a second predetermined wavelength and a wavelength region of the broadband light beam that is equal to or less than the second predetermined wavelength, wherein the first predetermined wavelength is a wavelength at which an intensity of the one of the long-wavelength light beams is equal to or greater than 10% of the peak intensity thereof and at which an intensity of the other long-wavelength light beam is equal to or greater than 10% of the peak intensity thereof, and wherein the second predetermined wavelength is a wavelength between the peak wavelength of the other long-wavelength light beam and the peak wavelength of the broadband light beam, and is a wavelength at which an intensity of the other long-wavelength light beam is equal to or greater than 10% of the peak intensity thereof, and at which an intensity of the broadband light beam is equal to or greater than 10% of the peak intensity thereof.

With the present invention, the long-wavelength light beam emitted from the long-wavelength light source and the broadband light beam that is emitted from the broadband light source and that has a spectrum that reaches the red wavelength region are multiplexed into a single beam by the multiplexing portion, and thus, the illumination light beam whose spectrum has no truncation at least in the green-to-red wavelength region is generated.

In this case, the long-wavelength light beam and the broadband light beam that have been multiplexed by the multiplexing portion have high enough intensities, which are equal to or greater than 10% of the respective peak intensities, in a wavelength region between the peak wavelength of the long-wavelength light beam and the peak wavelength of the broadband light beam. By doing so, it is possible to generate an illumination light beam that has good spectral characteristics with a low level of wavelength truncation and with which it is possible to ensure a better color reproduction.

Furthermore, when illuminating an object whose spectral reflectance is not constant, particularly in the red wavelength region, it is possible to more accurately express the tint of the object.

Note that, in this specification, the "red wavelength region" refers to a wavelength region that is from approximately 580 nm to approximately 760 nm, and that includes orange color. The "green wavelength region" refers to a wavelength region that is from approximately 500 nm to approximately 580 nm. The "blue wavelength region" refers to a wavelength region that is from approximately 380 nm to approximately 500 nm, and that includes purple color.

In the above-described invention, it is preferable that the broadband light beam have the peak wavelength in a range from 500 nm to 580 nm.

By doing so, it is possible to ensure a greater spectrum intensity of the illumination light beam, particularly in the green-to-red wavelength region, and thus, it is possible to achieve better spectral characteristics.

The above-described invention may be provided with at least two short-wavelength light sources that individually emit short-wavelength light beams that have peak wavelengths, which are different from each other, in a blue wavelength region, wherein the multiplexing portion multiplexes a wavelength region, which is greater than a third predetermined wavelength in the blue wavelength region, of one of the short-wavelength light beams having a peak wavelength on a longer-wavelength side, and a wavelength region, which is equal to or less than the third predetermined wavelength, of the other short-wavelength light beam having a peak wavelength on a shorter-wavelength side, and the third predetermined wavelength is a wavelength at which an intensity of the one of the short-wavelength light beams is equal to or greater than 10% of the peak intensity thereof and at which an intensity of the other short-wavelength light beam is equal to or greater than 10% of the peak intensity thereof.

By doing so, when illuminating an object whose spectral reflectance is not constant, particularly in the blue wavelength region, it is possible to more accurately express the tint of the object.

The above-described invention may be provided with an intensity-ratio adjusting portion that adjusts an intensity ratio of light beams multiplexed by the multiplexing portion.

By doing so, when capturing, by using an image-acquisition element, an image of an object illuminated with the illumination light beam, it is possible to optimize spectral characteristics of the illumination light beam with respect to spectral sensitivity characteristics of the image-acquisition element.

REFERENCE SIGNS LIST 1 light-source device
21 blue LED (short-wavelength light source)
22 green LED (broadband light source)
23 red LED (long-wavelength light source)
24 purple LED (short-wavelength light source)
25 orange LED (long-wavelength light source)
31, 32, 33, 34 dichroic filter (multiplexing portion)
4 collimator lens
5 converging lens
6 cover glass
7 light guide

The invention claimed is:

1. A light-source device comprising:
   at least two long-wavelength light sources that individually emit long-wavelength light beams that have peak wavelengths, which are different from each other, in a red wavelength region;
   a single broadband light source that emits a broadband light beam that includes a green wavelength region from 500 nm to 580 nm, that has a peak wavelength in a region that is equal to or less than 580 nm, and that has, on a long-wavelength side, a wavelength region that overlaps with a wavelength region of the long-wavelength light beam on a short-wavelength side; and
   a multiplexing portion that multiplexes a wavelength region, which is greater than a first predetermined wavelength in the red wavelength region, of one of the long-wavelength light beams having a peak wavelength on a longer-wavelength side, and a wavelength region, which is equal to or less than the first predetermined wavelength, of the other long-wavelength light beam having a peak wavelength on a shorter-wavelength side, and that multiplexes a wavelength region of the other long-wavelength light beam that is greater than a second predetermined wavelength and a wavelength region of the broadband light beam that is equal to or less than the second predetermined wavelength,
   wherein the first predetermined wavelength is a wavelength at which an intensity of the one of the long-wavelength light beams is equal to or greater than 10% of the peak intensity thereof and at which an intensity of the other long-wavelength light beam is equal to or greater than 10% of the peak intensity thereof, and
   wherein the second predetermined wavelength is a wavelength between the peak wavelength of the other long-wavelength light beam and the peak wavelength of the broadband light beam, and is a wavelength at which an intensity of the other long-wavelength light beam is equal to or greater than 10% of the peak intensity thereof, and at which an intensity of the broadband light beam is equal to or greater than 10% of the peak intensity thereof.

2. The light-source device according to claim 1, wherein the broadband light beam has the peak wavelength in a range from 500 nm to 580 nm.

3. The light-source device according to claim 1, further comprising:
   at least two short-wavelength light sources that individually emit short-wavelength light beams that have peak wavelengths, which are different from each other, in a blue wavelength region,
   wherein the multiplexing portion multiplexes a wavelength region, which is greater than a third predetermined wavelength in the blue wavelength region, of one of the short-wavelength light beams having a peak wavelength on a longer-wavelength side, and a wavelength region, which is equal to or less than the third predetermined wavelength, of the other short-wavelength light beam having a peak wavelength on a shorter-wavelength side, and
   the third predetermined wavelength is a wavelength at which an intensity of the one of the short-wavelength light beams is equal to or greater than 10% of the peak intensity thereof and at which an intensity of the other short-wavelength light beam is equal to or greater than 10% of the peak intensity thereof.

4. The light-source device according to claim 1, further comprising:
   an intensity-ratio adjusting portion that adjusts an intensity ratio of light beams that are multiplexed by the multiplexing portion.

* * * * *

UNITED STATES PATENT AND TRADEMARK OFFICE
CERTIFICATE OF CORRECTION

| | |
|---|---|
| PATENT NO. | : 10,531,789 B2 |
| APPLICATION NO. | : 15/433584 |
| DATED | : January 14, 2020 |
| INVENTOR(S) | : Ryo Machida |

It is certified that error appears in the above-identified patent and that said Letters Patent is hereby corrected as shown below:

On the Title Page

Column 1, item (30) under "Foreign Application Priority Data", delete "Aug. 20" and insert --Aug. 22--.

Signed and Sealed this
Twelfth Day of May, 2020

Andrei Iancu
*Director of the United States Patent and Trademark Office*